United States Patent [19]

Evans

[11] Patent Number: 4,481,214
[45] Date of Patent: Nov. 6, 1984

[54] 4-ACYLAMINOBENZOPYRANS USEFUL AS ANTI-HYPERTENSIVE AGENTS

[75] Inventor: John M. Evans, Roydon, England

[73] Assignee: Beecham Group p.l.c., England

[21] Appl. No.: 496,174

[22] Filed: May 19, 1983

[30] Foreign Application Priority Data

May 21, 1982 [GB] United Kingdom ................ 8214821
Jan. 15, 1983 [GB] United Kingdom ................ 8301088

[51] Int. Cl.$^3$ .................... C07D 311/02; A61K 31/35
[52] U.S. Cl. ..................................... 424/283; 549/404; 549/399; 549/345
[58] Field of Search .................. 549/399, 404, 345; 424/283

[56] References Cited

U.S. PATENT DOCUMENTS

| 4,048,317 | 9/1977 | Watts | 549/399 |
| 4,062,870 | 12/1977 | Watts | 549/399 |
| 4,107,317 | 8/1978 | Watts | 549/399 |
| 4,110,347 | 8/1978 | Watts | 549/399 |
| 4,119,643 | 10/1978 | Watts | 549/399 |
| 4,203,895 | 5/1980 | Parcell et al. | 549/399 |
| 4,251,537 | 2/1981 | Evans | 549/399 |
| 4,334,067 | 6/1982 | Ohno et al. | 549/399 |
| 4,363,811 | 12/1982 | Evans et al. | 548/525 |
| 4,366,163 | 12/1982 | Evans et al. | 546/196 |
| 4,391,815 | 7/1983 | Evans | 549/399 |
| 4,446,113 | 5/1984 | Evans et al. | 424/267 |

FOREIGN PATENT DOCUMENTS 46652  3/1982  European Pat. Off. ............ 549/399

OTHER PUBLICATIONS

Bui et al., Chem. Abstr., 91, 39,260p, (1979).
Lap et al., Aust. J. Chem., 1979, 32, pp. 619–636.

*Primary Examiner*—Nicky Chan
*Attorney, Agent, or Firm*—Jacobs & Jacobs

[57] ABSTRACT

Compounds of formula (I):

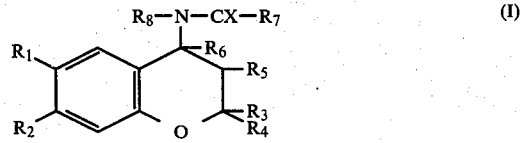

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together with the carbon atom to which they are attached are $C_{2-5}$ polymethylene;
either $R_5$ is hydroxy, $C_{1-6}$ alkoxy or $C_{2-7}$ acyloxy and $R_6$ is hydrogen or $R_5$ and $R_6$ together are a bond;
$R_7$ is hydrogen, $C_{1-6}$ alkyl optionally substituted by hydroxy, $C_{1-6}$ alkoxy, $C_{1-6}$ alkoxycarbonyl or carboxy, or $C_{1-2}$ alkyl substituted by halogen, or $C_{2-6}$ alkenyl;
$R_8$ is hydrogen or $C_{1-6}$ alkyl; and
X is oxygen or sulphur; the $R_8$—N—CX—$R_7$ group being trans to the $R_5$ group when $R_5$ and $R_6$ together are not a bond; or, when one or the other of $R_1$ and $R_2$ is an amino or an amino-containing group, a pharmaceutically acceptable salt thereof, having anti-hypertensive activity.

20 Claims, No Drawings

4-ACYLAMINOBENZOPYRANS USEFUL AS ANTI-HYPERTENSIVE AGENTS

The present invention relates to novel benzopyrans having pharmacological activity, to a process and intermediates for preparing them, to pharmaceutical compositions containing them, and to their use in the treatment of mammals.

U.S. Pat. No. 4,110,347 discloses compounds having blood pressure lowering activity which are of formula (A'):

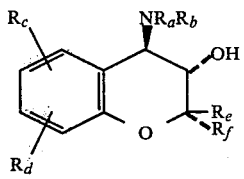

and acid addition salts thereof wherein, $R_a$ is a hydrogen atom or a $C_{1-9}$ hydrocarbon group optionally substituted by a hydroxyl or $C_{1-6}$ alkoxyl groupd; $R_b$ is a hydrogen atom or $C_{1-6}$ alkyl group, or $NR_aR_b$ is a 3-8 membered heterocyclic group optionally substituted by one or two methyl groups; $R_c$ is a hydrogen or halogen atom or a $C_{1-6}$ alkyl, $C_{2-6}$ alkenyl, $C_{1-6}$ alkoxy, $C_{2-6}$ alkenoxyl, $C_{1-6}$ alkylthio, hydroxyl, amino, $C_{1-6}$ alkylamino, $C_{1-6}$ dialkylamino, nitro, trifluoromethyl, $C_{2-7}$ acylamino, $C_{1-6}$ alkoxysulphonylamino, carboxyl, nitrile or $AOR_g$, $ASR_g$, $ASO_2R_g$, $ANHR_g$, $ANR_gCOR_h$, $ANR_gSO_2R_h$ or $ANR_gCO_2R_h$ group, in which A is an alkylene group of 1-4 carbon, $R_g$ is an alkyl group of 1-4 carbon atoms, and $R_h$ is an alkyl group of 1 to 4 carbon atoms; and $R_d$ is a hydrogen or halogen atom or methyl or methoxy, or $R_c$ together with $R_d$ forms a —CH=CH—CH=CH—, —NH—CH=CH—, —CH$_2$—CH$_2$—CH$_2$—CH$_2$— or —CH$_2$—CH$_2$—CH$_2$—CO— system; $R_e$ is a hydrogen atom or a $C_{1-6}$ alkyl or phenyl group; and $R_f$ is a hydrogen atom or a $C_{1-6}$ alkyl or phenyl group.

U.S. Pat. No. 4,251,532 discloses compounds having useful anti-hypertensive activity, which are of formula (B'):

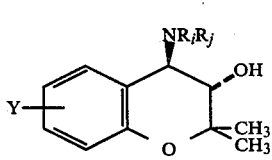

wherein $R_i$ is a hydrogen atom or an alkyl group of up to 4 carbon atoms optionally substituted by a chlorine or bromine atom or by a hydroxyl group or by an alkoxyl group of up to 4 carbon atoms or by an acyloxy group of up to 4 carbon atoms and $R_j$ is a hydrogen atom or an alkyl group of up to 4 carbon atoms or $R_i$ is joined to $R_j$ so that together with the nitrogen atom to which they are attached they form a 5-, 6- or 7-membered heterocyclic ring which is optionally substituted by methyl; Y is a group $COR_k$, $CO_2R_k$, $SOR_k$, $SO_2R_k$, $SOOR_k$, $SO_2OR_k$, $CH(OH)R_k$, $C(R_k)$=NOH, $C(R_k)$=NNH$_2$, CONH$_2$, CONR$_1$R$_m$, SONR$_1$R$_m$ or SO$_2$NR$_1$R$_m$ where $R_k$ and $R_1$ are each independently a hydrocarbon group of up to 8 carbon atoms or such a group inertly substituted by a chlorine or bromine atom or by a hydroxyl group or by an alkoxyl group of 1-4 carbon atoms or by an acyloxy group of up to 4 carbon atoms or by 3 fluorine atoms attached to the same carbon atom and $R_m$ is a hydrogen atom or an alkyl group of up to 4 carbon atoms; and salts thereof and O-acyl derivatives thereof wherein the O-acyl moiety contains up to 18 carbon atoms.

European Patent Publications Nos. 28064 and 28449 describe compounds having blood pressure lowering activity, with low levels of unwanted cardiac effects, which compounds are of formula (C'):

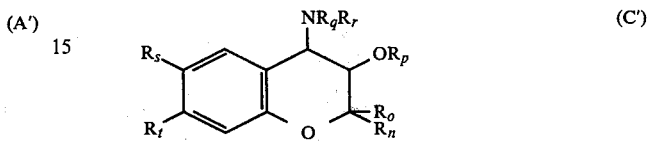

wherein:
$R_n$ is a hydrogen atom or a lower alkyl group;
$R_o$ is a hydrogen atom or a lower alkyl group;
$R_p$ is a hydrogen atom or a lower alkyl group;
$R_q$ is a hydrogen atom or a lower alkyl group;
$R_r$ is a lower alkyl or a substituted alkyl group; or
$R_q$ and $R_r$ are joined so that together with the nitrogen atom to which they are attached they form a 5-, 6- or 7-membered ring optionally containing an oxygen or sulphur atom;
one of $R_s$ and $R_t$ is an electron withdrawing group and the other is an electron donating group; and the NRqR$_r$ and OR$_p$ moieties are trans.

U.S. Pat. No. 4,119,643 discloses compounds having anti-hypertensive activity, which are of formula (D'):

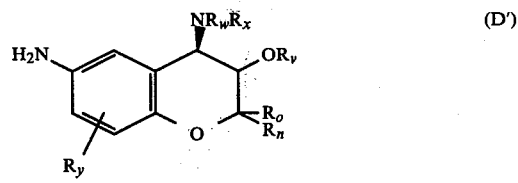

wherein:
$R_n$ and $R_o$ are as defined for formula (C');
$R_v$ is a hydrogen atom or —COR$_z$, wherein $R_a$ is a $C_{1-8}$ hydrocarbon group optionally substituted by halogen or hydroxy;
$R_w$ is a hydrogen atom or a $C_{1-4}$ alkyl group;
$R_x$ is a group —X—Y, wherein X is an alkylene group of 2 to 6 carbon atoms and Y is a halogen atom, or a OZ group, wherein Z is a $C_{1-7}$ hydrocarbon, methanesulphonyl, toluene-p-sulphonyl or phenylsulphonyl; and
$R_y$ is a hydrogen, fluorine or chlorine atom or a hydroxy, methoxy or methyl group.

A further class of benzopyrans have now been discovered which are characterised by the presence of a an acyclic carbonylamino- or thiocarbonylamino-containing group which substitutes the benzopyran in the 4-position. Moreover, such benzopyrans have been found to have blood pressure lowering activity.

Accordingly, the present invention provides a compound of formula (I):

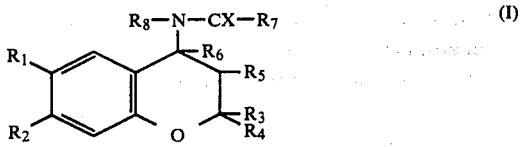

(I)

wherein:

either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkylthiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)-NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ are $C_{2-5}$ polymethylene;

either $R_5$ is hydroxy, $C_{1-6}$ alkoxy or $C_{2-7}$ acyloxy and $R_6$ is hydrogen or $R_5$ and $R_6$ together are a bond;

$R_7$ is hydrogen, or $C_{1-6}$ alkyl optionally substituted by hydroxy, $C_{1-6}$ alkoxy, $C_{1-6}$ alkoxycarbonyl or carboxy, or $C_{1-2}$ alkyl substituted by halogen, or $C_{2-6}$ alkenyl;

$R_8$ is hydrogen or $C_{1-6}$ alkyl; and

X is oxygen or sulphur; the $R_8$—N—CX—$R_7$ group being trans to the $R_5$ group when $R_5$ and $R_6$ together are not a bond; or, when one or the other of $R_1$ and $R_2$ is an amino or an amino-containing group, a pharmaceutically acceptable salt thereof.

When one of $R_1$ and $R_2$ is hydrogen, the other is preferably selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro or cyano. In particular, when one of $R_1$ and $R_2$ is hydrogen, the other is preferably nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{2-7}$ acyloxy and $R_6$ is hydrogen, a preferred class of $R_5$ is unsubstituted carboxylic acyloxy, such as unsubstituted aliphatic acyloxy or benzoyloxy. However, it is preferred that $R_5$ and $R_6$ together are a bond, or, in particular, $R_5$ is hydroxy and $R_6$ is hydrogen.

Examples of $R_7$, when $C_{1-6}$ alkyl, include methyl, ethyl and n- and iso-propyl. Preferably $R_7$, when $C_{1-6}$ alkyl, is methyl.

Examples of $R_7$, when $C_{1-6}$ alkyl substituted by hydroxy, include methyl or ethyl terminally substituted by hydroxy.

A sub-class of $R_7$, when $C_{1-6}$ alkyl substituted by $C_{1-6}$ alkoxy, is $C_{1-6}$ alkyl substituted by methoxy or ethoxy. Examples thereof include methyl or ethyl terminally substituted by methoxy or ethoxy.

A sub-class of $R_7$, when $C_{1-6}$ alkyl substituted by $C_{1-6}$ alkoxycarbonyl, is $C_{1-6}$ alkyl substituted by methoxycarbonyl or ethoxycarbonyl. Examples thereof include methyl or ethyl terminally substituted by methoxycarbonyl or ethoxycarboxy.

Examples of $R_7$, when $C_{1-6}$ alkyl substituted by carboxy, include methyl or ethyl terminally substituted by carboxy.

A sub-class of $R_7$, when $C_{1-2}$ alkyl substituted by halogen, is methyl or ethyl terminally substituted by chloro or bromo, in particular by chloro.

Examples of $R_7$, when $C_{2-6}$ alkenoyl, include vinyl, prop-1-enyl, prop-2-enyl, 1-methylinyl, but-1-enyl, but-2-enyl, but-3-enyl, 1-methylenepropyl, or 1-methylprop-2-enyl, in both their E and Z forms where stereoisomerism exists.

Examples of $R_8$ include hydrogen, methyl, ethyl, n- or iso-propyl. Preferably, $R_8$ is hydrogen or methyl, especially hydrogen.

Examples of a pharmaceutically acceptable salt of a compound of formula (I), when one or the other of $R_1$ and $R_2$ is an amino or an amino-containing group, include the hydrochloride and hydrobromide salts.

Preferably, a compound of formula (I) is in substantially pure form.

The compounds of formula (I), wherein $R_5$ is hydroxy, $C_{1-6}$ alkoxy or $C_{2-7}$ acyloxy and $R_6$ is hydrogen, are disymmetric and, therefore, can exist as stereoisomers. The present invention extends to all such stereoisomers individually and as mixtures, such as racemic modifications.

Examples of compounds of formula (I) include the compounds prepared in the Examples hereinafter. Of these, those that are particularly preferred include:

trans-4-N-acetylamino-6-cyano-3,4-dihydro-2,2-dimethyl-2H-benzo[b]pyran-3-ol;

trans-4-N-acetylamino-6-cyano-3,4-dihydro-2,2-dimethyl-2H-benzo[b]pyran-3-yl acetate;

trans-4-N-acetylamino-6-acetyl-3,4-dihydro-2,2-dimethyl-2H-benzo[b]pyran-3-ol; and trans-4,7-bis(acetylamino)-6-nitro-3,4-dihydro-2,2-dimethyl-2H-benzo[b]pyran-3-ol.

The present invention also provides a process for preparing a compound of formula (I), which comprises acylating a compound of formula (II):

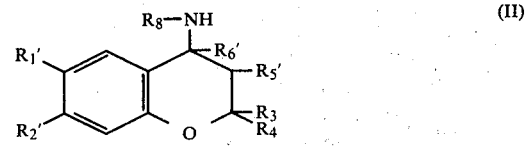

(II)

wherein $R_1'$ and $R_2'$ are $R_1$ and $R_2$, as defined hereinbefore, or a group or atom convertible thereto, $R_3$, $R_4$ and $R_8$ are as defined hereinbefore, $R_5'$ is hydroxy, $C_{1-6}$ alkoxy or $C_{2-7}$ acyloxy and $R_6'$ is hydrogen, the $R_8NH$ group being trans to the $R_5'$ group, with an acylating agent of formula (III):

$$R_7\text{—CO—}L_1 \qquad (III)$$

wherein $R_7$ is as defined hereinbefore and $L_1$ is a leaving group; in the case where $R_1'$ or $R_2'$ is a group or atom convertible into $R_1$ or $R_2$, converting the group or atom into $R_1$ or $R_2$; optionally converting $R_1$, $R_2$ or $R_5$ in the resulting compound of formula (I) into another $R_1$, $R_2$ or $R_5$; in the case where $R_5$ and $R_6$ in the resulting compound of formula (I) are hydroxy and hydrogen respectively, optionally dehydrating the compound to give another compound of formula (I), wherein $R_5$ and $R_6$ together are a bond; optionally thaiting the $R_8$—N—CO—$R_7$ group in the resulting compound of formula (I) to give another compound of formula (I), wherein X is sulphur; and, when one or the other of $R_1$ and $R_2$ in the resulting compound of formula (I) is amino or an amino-containing group, optionally forming a pharmaceutically acceptable salt.

The leaving group ($L_1$) is a group that is displaceable by a primary or secondary amino nucleophile. Examples of such a group include $C_{2-9}$ acyloxy, such as mesyloxy, tosyloxy, triflate and $C_{1-4}$ alkylcarbonyloxy, and halogen, such as chloro and bromo. When the leaving group ($L_1$) is either of these examples, the acylating agent of formula (III) is either an acid anhydride or an acid halide. When it is acid anhydride, it may be a mixed or simple anhydride. If it is a mixed anhydride, it may be prepared in situ from a carboxylic acid and an acid halide.

When the acylating agent of formula (III) is in acid anhydride, the acylation of the compound of formula (II) is, preferably, carried out using the anhydride as the solvent in the presence of an acid acceptor, such as sodium acetate.

When the acylating agent of formula (III) is an acid halide, the acylation of the compound of formula (II) is, preferably, carried out in an aqueous medium, such as chloroform/water, in the presence of an acid acceptor, such as triethylamine, trimethylamine, pyridine, picoline or calcium, potassium or sodium carbonate.

When $R_5'$ in a compound of formula (II) is hydroxy, there is a risk of a side-reaction between the hydroxy group and the acylating agent of formula (III). It is, therefore, preferred that either $R_5'$ is $C_{2-7}$ acyloxy in a compound of formula (II) and, after reaction with the acylating agent of formula (III), is converted into hydroxy, as described hereinafter. It is however, even more preferred that the reaction is controlled such that only the amine, $R_8NH$—, is acylated, for example, by using a $C_{2-9}$ acyloxy group as the leaving group ($L_1$), in the acylating agent of formula (III) in the manner as previously described for an acid anhydride.

Conversions of an aromatic group into $R_1$ or $R_2$, as defined hereinbefore, are generally known in the art of aromatic chemistry. For example, it is preferred when carrying out the acylation of a compound of formula (II), first to protect any unsubstituted terminal amine, that may be present for $R_1$ or $R_2$, such as amino aminosulphinyl, aminosulphonyl or aminocarbonyl, and afterwards to convert the protected amino moiety into the required terminal amine. Examples of protecting agents include acyl groups, such as acetyl, which may be added and removed conventionally. If it is desired to protect a terminal amino moiety in the presence of a cyano group then a more appropriate method is to use a trifluoroacetyl protecting group which may be removed by mild hydrolysis or to use a benzyloxycarbonyl or a p-nitrobenzyloxycarbonyl protecting group which may be removed by mild catalytic hydrogenolysis.

If the optional thiation reaction is to be carried out in order to obtain a compound of formula (I), wherein one or the other of $R_1$ and $R_2$ is a carbonyl-containing group and X is sulphur, it is preferred to use in the acylation reaction the corresponding compound of formula (II), wherein $R_1'$ or $R_2'$ is a protected carbonyl-containing group, and after thiation to convert the protected carbonyl-containing group into the required carbonyl-containing group for $R_1$ or $R_2$. Without such protection, the additional carbonyl group may give rise to a competing side-reaction. Examples of preferred carbonyl protecting groups include ketalising agents, which may be added and removed in conventional manner.

Examples of an optional conversion of $R_1$ or $R_2$ in the resulting compound of formula (I) into another $R_1$ or $R_2$, as defined hereinbefore, include the optional conversion of an α-hydroxyethyl group into acetyl by oxidation, the optional conversion of a chloro atom into an amino group by amination, the optional conversion of an amino group into an amino group substituted by one or two $C_{1-6}$ or by $C_{2-7}$ alkanoyl, or the optional conversion of a hydrogen atom into a nitro group by nitration.

Examples of an optional conversion of $R_5$ in a compound of formula (I) into another $R_5$ are generally known in the art. For example, when $R_5$ is hydroxy, it may be alkylated using an alkyl iodide in an inert solvent, such as toluene, in the presence of a base, such as potassium hydroxide, or it may be acylated using a carboxylic acid chloride or anhydride in a non-hydroxylic solvent in the presence of a condensation promoting agent, such as dicyclohexylcarbodiimide. Alternatively, when $R_5$ is $C_{2-7}$ acyloxy or it may be converted into hydroxy by conventional hydrolysis with for example, dilute mineral acid.

The optional dehydration of a resulting compound of formula (I), wherein $R_5$ and $R_6$ are hydroxy and hydrogen respectively, into another compound of formula (I), wherein $R_5$ and $R_6$ together are a bond, may be carried out in accordance with conventional dehydration conditions, for example, by using a dehydrating agent, such as sodium hydride, in an inert solvent, such as dry tetrahydrofuran, at reflux temperature.

The optional thiation of the $R_8$—N—CO—$R_7$ group in a compound of formula (I) to give another compound of formula I, wherein X is sulphur, is, preferably, carried out with conventional thiation agents, such as hydrogen sulphide, phosphorous pentasulphide and Lawesson's reagent (p-methoxyphenylthiophosphine sulphide dimer). The use of hydrogen sulphide and phosphorus pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

The optional formation of a pharmaceutically acceptable salt, when one or the other of $R_1$ and $R_2$ in the resulting compound of formula (I) is amino or an amino-containing group, may be carried out conventionally.

A compound of formula (II) may be prepared by reacting a compound of formula (IV):

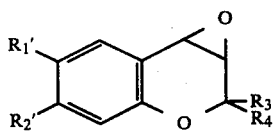

wherein $R_1'$, $R_2'$, $R_3$ and $R_4$ are as defined hereinbefore, with a compound of formula (V):

    (V)

or a salt thereof, wherein $R_8$ is as defined hereinbefore; and optionally converting the hydroxy group for $R_5'$ in the resulting compound of formula (II) into a $C_{1-6}$ alkoxy or $C_{2-7}$ acyloxy group.

The reaction is normally carried out in a solvent, such as a $C_{1-4}$ alcohol, in particular methanol, ethanol or propanol at an ambient or an elevated temperature, for example 12° to 100° C. The reaction proceeds particularly smoothly if carried out in ethanol under reflux.

The resulting compound of formula (II) may be removed from the reaction mixture by removal of the solvent, for example, by evaporation under reduced pressure. Any epoxide impurity may be removed conventionally, for example by chromatography.

The optional conversion of the hydroxy group for $R_5'$ in the resulting compound of formula (II) into a $C_{1-6}$ alkoxy or $C_{2-7}$ acyloxy group may be carried out as described hereinbefore in relation to the corresponding conversion of $R_5$ in a compound of formula (I).

A compound of formula (IV) may be prepared, preferably in situ, by reacting a compound of formula (VI):

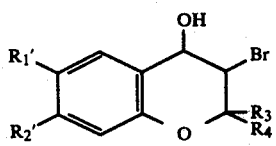

wherein $R_1'$, $R_2'$, $R_3$ and $R_4$ are as defined hereinbefore and the hydroxy group is trans to the bromo atom, with a base, such as potassium hydroxide, in a solvent, such as ether or aqueous dioxan.

Compounds of formula (VI) are known and may be prepared in accordance with any appropriate known process, for example, by the process described in the aforementioned U.S. patents and European patent publications. Schematically, such process can be depicted thus.

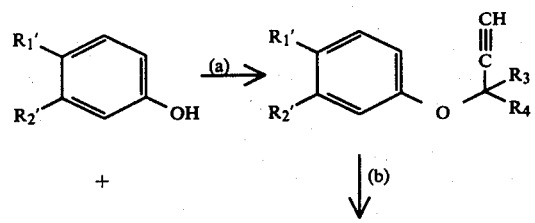

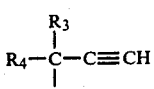

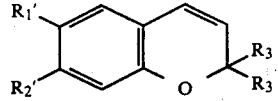

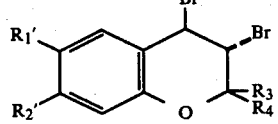

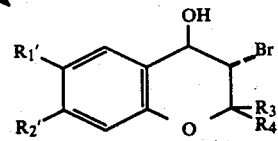

(a) Room temperature; NaOH/40% benzyltrimethylammonium hydroxide in methanol;
(b) Heat in o-dichlorobenzene;
(c) N—bromosuccinimide/dimethylsulphoxide/water;
(d) Bromine in carbon tetrachloride; and
(e) Acetone/water.

The above process may produce mixtures of compounds during reaction (b) owing to the two sites available for ring formation. It is therefore advisable to remove any of the undesired compound by, for example, chromatography, before reaction (c) or (d).

As mentioned previously, the compounds of formula (I) exist in optically active forms, and the processes of the present invention produce mixtures of such forms. The individual isomers may be separated one from the other by chromatography using a chiral phase.

It is preferred that the compounds of formula (I) are isolated in substantially pure form.

The compounds of formula (II) and (V) are also known or can be prepared analogously to the preparation of known compounds.

A number of the compounds of formula (II) are known from the aforementioned U.S. Patents and European Patent publications. However, there is a novel class of compounds falling within formula (II) which are of formula (VII):

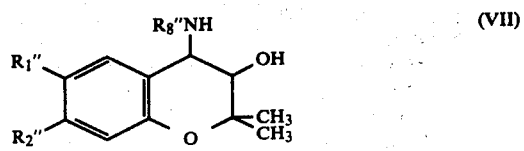

wherein either one of $R_1''$ and $R_2''$ is hydrogen and the other is $C_{1-6}$ alkylcarbonyl, $C_{1-6}$ alkoxycarbonyl, $C_{1-6}$ alkylcarbonyloxy, $C_{1-6}$ alkylhydroxymethyl or cyano or one of $R_1''$ and $R_2''$ is $C_{1-6}$ alkylcarbonyl, nitro or cyano and the other is amino and $R_8''$ is methyl or ethyl; and $R_8''$ NH group being trans to the hydroxy group.

A preferred sub-class of compounds of formula (VII) are those wherein the alkyl groups or alkyl moieties of alkyl-containing groups are methyl or ethyl.

The compounds of formula (VII) are particularly useful intermediates, which can be prepared as described hereinbefore and which represent part of the present invention.

As mentioned previously, the compounds of formula (I) have been found to have blood-pressure lowering activity. They are therefore useful in the treatment of hypertension.

The present invention accordingly provides a pharmaceutical composition which comprises a compound of this invention and a pharmaceutically acceptable carrier. In particular, the present invention provides an anti-hypertensive pharmaceutical composition which comprises an anti-hypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vaials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 5 to 200 mg for a 70 kg human adult and more particularly from 10 to 100 mg.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and $\beta$-blocking agents.

The present invention further provides a compound of the invention for use in the treatment of hypertension.

The present invention yet further provides a method of treating hypertension in mammals including man, which comprises administering to the suffering mammal an anti-hypertensive effective amount of a compound or a pharmaceutical composition of the invention.

The following descriptions relate to the preparation of intermediates and the following examples relate to the preparation of a compound of formula (I).

DESCRIPTION 1

6-Cyano-3,4-dihydro-2,2-dimethyl-3,4-epoxy-2H-benzo[b]-pyran

4-Cyanophenol (19.60 g), sodium hydroxide (9.90 g), 40% benzyltrimethylammonium hydroxide in methanol (34.50 g) and 3-methyl-3-chlorobutyne (25.50 g) were stirred in water (150 ml) and dichloromethane (150 ml) for 5.5 days at room temperature. After separation of the layers, the aqueous layer was extracted twice with chloroform, and the combined organic phase evaporated leaving a gum which was taken up in ether and washed three times with 10% sodium hydroxide solution and with water before drying over magnesium sulphate. Removal of drying agent and solvent gave a viscous liquid having absorptions in the IR (film) at 2100, 2220, 3290 cm$^{-1}$. This liquid (20.91 g) was heated in o-dichlorobenzene (40 ml) at reflux temperature for 1.5 hours under nitrogen. After distillation of the solvent the fraction boiling at 110°-114°/0.02 mmHg (16.57 g) was collected, which on standing formed a low melting solid, having an IR absorption at 2230 cm$^{-1}$. (See M. Harfenist and E. Thom, *J. Org. Chem.*, 37, 841 (1972) who quote m.p. 36°-37°).

Addition to this 6-cyanochromene (16.50 g) dissolved in dimethyl sulphoxide (150 ml) containing water (3.24 ml), of N-bromosuccinimide (31.90 g) with vigorous stirring and cooling, followed by dilution with water and extraction via ethyl acetate gave a mixture which was boiled in acetone (300 ml) and water (100 ml) for 5 hours to hydrolyse the small amount of 3,4-dibromide present. Evaporation of solvents gave 6-Cyano-trans-3-bromo-3,4-dihydro-2,2-dimethyl-2H-benzo[b]pyran-4-ol as white crystals (24.37 g). A small sample had m.p. 128°-128.5° from 60°-80° petroleum ether, nmr (CDCl$_3$).

1.43 (3H), 1.62 (3H), 7.48 (1H, exchangeable) 4.07 (1H, d, J=9), 4.87 (1H, d, J=9), 6.80 (1H, d, J=8), 7.43 (1H, q, J=8 2), 7.78 (1H, d, J=2). Anal. Calcd. for C$_{12}$H$_{12}$NO$_2$Br: C, 51.07; H, 4.26; N, 4.96; Br, 28.37. Found: C, 50.95; H, 4.38; N, 5.03; Br, 28.39%.

The bromohydrin (24.30 g) was stirred with sodium hydroxide pellets (5.00 g) in water (250 ml) and dioxan (200 ml) for 3 hours at room temperature. The solvents were removed by distillation under high vacuum and the residue taken up in ether and washed with water and brine before drying over magnesium sulphate. Removal of drying agent and solvent and gave crude 6-cyano-3,4-dihydro-2,2-dimethyl-3,4-epoxy-2H-benzo[b]pyran (16.02 g) as a gum, having an absorption at 2230 cm$^{-1}$ in the IR and Nmr (CCl$_4$) 1.26 (3H), 1.54 (3H), 3.40 and 3.80 (each 1H, d, J=4), 6.77 (1H, d, J=8), 7.43 (1H, q, J=8, 2), 7.58 (1H, d, J=2).

DESCRIPTION 2

7-Acetamido-3,4-dihydro-2,2-dimethyl-6-nitro-3,4-epoxy-2H-benzo-[b]pyran 2,2-Dimethyl-7-nitro-2H-benzo[b]pyran (40.00 g, the preparation of which is disclosed in British Patent No. 1,548,222), glacial acetic acid (200 ml), acetic anhydride (120 ml) and electrolytic iron powder (88 g) were stirred and heated at 120° C. for 16 hours. Dilution with water, extraction via chloroform followed by washing of the organic layer with water and sodium bicarbonate solution, drying evaporation etc., gave a crude gum which was chromatographed on a silica gel column using ethyl acetate −60°-80° petroleum ether mixtures in a gradient elution technique. Fractions homogeneous by TLC were combined and recrystallised from 60°-80° petroleum ether to give 7-acetamido-2-,2-dimethyl-2H-benzo[b]pyran (5.27 g) as white needles of mp 80°-81° C.; nmr (CDCl$_3$) 1.39 (6H), 2.12 (3H), 5.48 (1H, d, J=10), 6.21 (1H, d, J=10), 6.76-7.34 (3H, m), 8.95 (1H). Anal. Calcd for C$_{13}$H$_{15}$NO$_2$; C, 71.87; H, 696; N, 6.45. Found: C, 72.00; H, 7.11; N, 6.23%.

To this acetamidobenzopyran (5.17 g) dissolved in glacial acetic acid (29 ml) was added fuming nitric acid (1.70 ml) dropwise with stirring at 0° C. Dilution with water and extraction via ethyl acetate gave a yellow solid (6.63 g) which was chromatographed on a silica gel column using ethyl acetate −60°-80°, petroleum ether mixtures in a gradient elution technique. The least polar component was recrystallised as yellow needles of 7-acetamido-2,2-dimethyl-6-nitro-2H-benzo[b]pyran (1.80 g) of mp 148°-150° C. from ethanol; nmr (CDCl$_3$) 1.47 (6H), 2.28 (3H), 5.72 (1H, d, J=10), 6.33 (1H,d,J=10) 7.93 (1H), 8.25 (1H). Anal. Calcd for C$_{13}$H$_{14}$N$_2$O$_4$: C, 59.54; H, 5.38; N, 10.69. Found: C, 59.61; H, 5.41; N, 10.69%.

To this nitro compound (1.80 g) dissolved in dimethyl sulphoxide (25 ml) and water (0.25 ml) was added N-bromosuccinimide (2.47 g) in one portion and with vigorous stirring. After dilution with water, extraction via ethyl acetate gave a yellow solid (2.59 g). A small portion recrystallised from ethanol gave 7-acetamido-trans-3-bromo-3,4-dihydro-2,2-dimethyl-6-nitro-2H-benzo[b]pyran-4-ol as yellow needles mp 205°–206°; n.m.r. (CDCl$_3$) 1.45 (3H), 1.63 (3H), 2.25 (3H), 4.07 (1H, d, J=9), 4.78 (1H, d, J=9), 8.08 (1H), 8.41 (1H), 10.31 (1H). Anal. Calcd for C$_{13}$H$_{15}$BrN$_2$O$_5$: C, 43.45; H, 4.18; N, 7.80; Br, 22.28. Found C, 43.99; H, 4.39; N, 8.35; Br 22.02%.

This bromohydrin (2.50 g), sodium hydroxide pellets (4.00 g), water (20 ml) and dioxan (100 ml) were stirred at room temperature for 40 min. Dilution with water (1 liter) and extraction via ethyl acetate gave a crude yellow solid (2.00 g).

DESCRIPTION 3

6-Acetamido-3,4-dihydro-2,2-dimethyl-7-nitro-3,4-epoxy-2H-benzo[b]pyran

To 6-Acetamido-2,2-dimethyl-7-nitro-2H-benzo[b]pyran (10.78 g, the preparation of which was disclosed in U.K. Pat. No. 1,548,222) dissolved in dimethyl sulphoxide (100 ml) containing water (1.48 ml), was added freshly recrystallised N-bromosuccinimide (14.59 g) with vigorous stirring. Dilution with water (700 ml) and filtration and drying of the solid obtained gave 6-Acetamido-trans-3-bromo-3,4-dihydro-2,2-dimethyl-7-nitro-2H-benzo[b]pyran-4-ol as a yellow solid (14.06 g). A small portion recrystallised from ethanol had m.p. 198°–200°; nmr (CDCl$_3$/DMSOd$_6$) δ 1.62 (3H), 1.79 (3H), 2.37 (3H), 4.27 (1 exchangeable H, m) overlapped with 4.35 (1H, d, J=9), 5.01 (1H, d, J=9), 7.83 (1H), 8.56 (1H), 10.02 (1 exchangeable H, m). Anal. Calcd for C$_{13}$H$_{15}$N$_2$O$_5$Br: C, 43.47; H, 4.21; N, 7.80. Found: C, 43.70; H, 4.37; N, 7.46%.

This bromohydrin (14.02 g), sodium hydroxide pellets (14.00 g) dioxan (750 ml) and water (140 ml) were stirred at room temperature during 3 hours. Evaporation to half volume and addition of water (1 L) and extraction via ethyl acetate (3×500 ml), and washing of the combined organic layers with water and brine, drying and solvent removal gave a red gummy solid (11.12 g). Recrystallisation from ethanol gave 6-acetamido-3,4-dihydro-2,2-dimethyl-3,4-epoxy-7-nitro-2H-benzo[b]pyran as a yellow solid (5.92 g) of m.p. 156°–158°; nmr δ (CDCl$_3$) 1.27 (3H), 1.60 (3H), 2.25 (3H), 3.53 (2H, d, J=4), 3.98 (1H, d, J=4), 7.62 (1H), 8.77 (1H), 10.05 (1H). Manipulation of the mother liquors gave an additional crop of epoxide (0.74 g). Anal. Calcd for C$_{13}$H$_{14}$N$_2$O$_5$: C, 56.11; N, 5.07; N, 10.07. Found: C, 55.92; H, 5.27; N, 9.82%.

DESCRIPTION 4

6-Chloro-3,4-dihydro-2,2-dimethyl-trans-3-bromo-4-hydroxy-2H-benzo[b]pyran

The title compound was prepared analogously to the preparation of the 3-bromo-4-hydroxy compound of Description 1 giving a crude crystalline solid.

| NMR (CDCl$_3$): δ | 1.35 (3H, s) |
| | 1.53 (3H, s) |
| | 3.22 (2H, m) |
| | 4.00 (1H, d, J = 9Hz) |
| | 4.77 (1H, d, J = 9Hz) |
| | 6.51 (1H, d, J = 8Hz) |
| | 7.03 (1H, q, J = 8, 2Hz) |
| | 7.30 (1H, narrow m). |

DESCRIPTION 5

6-Chloro-3,4-dihydro-2,2-dimethyl-3,4-epoxy-2H-benzo[b]pyran

The crude crystalline solid (10.27 g) of Description 4 was dissolved in dimethyl sulphoxide (50 ml) and treated with sodium hydride (1.06 g, 80% dispersion on oil) over a period of an hour. The resulting material was used as such in Example 9 after addition of water and extraction with ethyl acetate.

DESCRIPTION 6

Preparation of 6-acetamido-trans-4-amino-3,4-dihydro-2,2-dimethyl-7-nitro-2H-benzo[b]pyran-3-ol

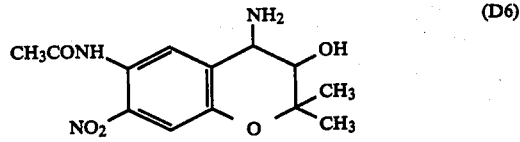
(D6)

6-Acetamido-3,4-epoxy-3,4-dihydro-2,2-dimethyl-7-nitro-2H-benzo[b]pyran (1.0 g) was dissolved in dry ethanol (150 ml) and saturated with ammonia during 3 h, with cooling. The reaction mixture was stirred at room temperature for 5 days and evaporated. The crude residue was purified on the chromatotron (80% ethyl acetate-pentane to 20% methanol-ethyl acetate gradient elution), to give the title compound (410 mgm). A small portion was converted to the hydrochloride salt and recrystallised from ethanol-diethyl ether, with m.p. 258°–261° C.

Anal. Calc. for C$_{13}$H$_{18}$N$_3$O$_5$Cl: C, 47.0; H, 5.47; N, 12.66; Cl, 10.72. Found: C, 46,92; H, 5.58; N, 12,19; Cl, 10.74%.

DESCRIPTION 7

Preparation of 7-acetamido-trans-4-amino-3,4-dihydro-2,2-dimethyl-6-nitro-2H-benzo[b]pyran-3-ol

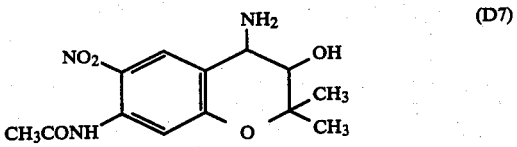
(D7)

7-Acetamido-3,4-epoxy-3,4-dihydro-2,2-dimethyl-6-nitro-2H-benzo[b]pyran (0.76 g,) was dissolved in dry ethanol and saturated with dry ammonia, and stirred at room temperature for 21 hr. Evaporation gave a crude mixture which was purified on the chromatotron (using pentane-ethyl acetate in a gradient elution), to give the title compound (280 mg).

EXAMPLE 1

Trans-4-N-acetylethylamino-6-cyano-3,4-dihydro-2,2-dimethyl-2H-benzo[b]pyran-3-ol (Compound 1)

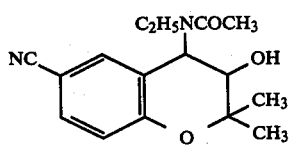

6-Cyano-3,4-dihydro-2,2-dimethyl-3,4-epoxy-2H-benzo-[b]pyran (1.01 g) was stirred in 30% ethylamine in ethanol solution (10 ml) for four days at room temperature. Evaporation gave a brown gum (1.20 g) which solidified on standing.

This solid (423 mg), anhydrous sodium acetate (140 mg) and acetic anhydride (8 ml) was warmed for 3 hrs at 35°–40° C. with exclusion of moisture. On cooling the mixture was poured into ice-water and extracted with ethyl acetate. This was washed with water and brine before drying over MgSO$_4$, and evaporation gave an oil (410 mg) which was chromatographed using a chromatotron (2 mm silica gel HF$_{254}$ plate; solvent flow 6 ml/min). Elution with 40% ethyl acetate-petroleum ether gave, in addition, to starting material, the title compound (230 mg) which was recrystallised from ethyl acetate (210 mg), m.p. 168°–170° C.

IR (Nujol) 3300, 2230, 1620 cm$^{-1}$

Mass Spectrum (E.I.) M$^+$ at M/z 288

Anal. C$_{16}$H$_{20}$N$_2$O$_3$ requires: C, 66.65; H, 6.99; N, 9.72; C, 66.76; H, 7.03; N, 9.73%.

EXAMPLE 2

Trans-4-N-acetylamino-6-cyano-3,4-dihydro-2,2-dimethyl-2H-benzo[b]pyran-3-ol (Compound 2)

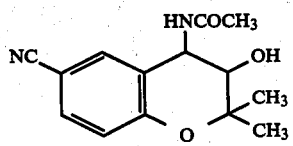

6-Cyano-3,4-dihydro-2,2-dimethyl-3,4-epoxy-2H-benzo[b]pyran (10.0 g) was stirred in ethanol (20 ml) and the ammonium hydroxide solution (50 ml) for 4 days at room temperature. Evaporation gave a yellow gum (10.1 g) which solidified on standing.

This solid (1.0 g), anhydrous sodium acetate (2.00 g) and acetic anhydride (20 ml) were stirred for 5 hours at room temperature. The mixture was poured into water and extracted with ethyl acetate. This was washed with water and brine, and dried over MgSO$_2$. Removal of drying agent, and evaporation gave a solid which was chromatographed using a chromaton (2 mm silica gel HF$_{25}$ plate, solvent flow 6 ml/min elution with ethyl acetate-pentane using a gradient technique gave a fraction which contained the crude title compound. Recrystallisation of this material from ethyl acetate gave trans-4-N-acetylamino-6-cyano-3,4-dihydro-2,2-dimethyl-2H-benzo[b]pyran-3-ol (208 mgm) as crystals of m.p. 203-250.

NMR (CDCl$_3$-DMSOd$_6$) 1.25 (3H,s), 1.47 (3H, s), 2.08 (3H, s), 3.60 (q, J=9, 5 Hz), 4.93 (q, J=9, 8 Hz), 5.24 (d, J=5 Hz), 6.86 (d, J=8 Hz), 7.43 (q, J=8, 2 Hz) overlapping 7.50 (d, J=2 Hz) 8.00 (d, J=8 Hz).

Anal. C$_{14}$H$_{16}$N$_2$O$_3$ requires: C, 64.60; H, 6.20; N, 10.76; found: C, 64.51; H, 6.21; N, 10.78%.

EXAMPLE 3

Trans-6-cyano-3,4-dihydro-2,2-dimethyl-4-N-propenoylamino-2H-benzo[b]pyran-3-ol (Compound 6)

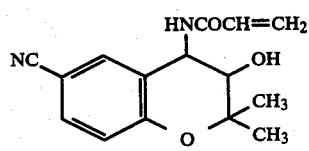

Trans-4-amino-3,4-dihydro-2,2-dimethyl-2H-benzo[b]pyran-3-ol (1.19 g, prepared by treatment of the corresponding 3,4-epoxide with ethanolic ammonium hydroxide), sodium hydroxide pellets (0.2 g) and water (10 ml) was stirred with chloroform (20 ml) under N$_2$ for 0.5 hr. Bromopropionyl chloride (0.51 ml) was added in one portion and the mixture stirred vigorously for 0.5 hr. Separation of the layers, was followed by further extraction of the aqueous with chloroform. The combined organic extracts were washed with water and brine before drying over MgSO$_4$. Filtration and evaporation of solvent gave the bromo amide as a pale yellow solid (1.10 g) having a molecular ion at m/z 334.0321 on mass spectrometric examination.

To a stirred suspension of sodium hydride (177 mg, 80% dispersion in oil) in dry tetrahydrofuran (20 ml) under nitrogen was added the crude amide (1.04 g) dissolved in dry tetrahydrofuran (20 ml) during 2 min. A white solid slowly formed as the mixture was stirred for 4.5 hours at room temperature. Addition of water and extraction via ethyl acetate with water and brine washing, followed by drying over MgSO$_4$, filtration and evaporation gave the title compound as crystals (240 mg) of mp 194°–195.5° C. from ethyl acetate.

NMR (CDCl$_3$ and DMSOd$_6$) 1.30 (3H, s), 1.50 (3H, s), 3.68 (1H, d, J=9 Hz), 4.83 (1H, brm-exchangeable with D$_2$O), 5.10 (1H, d, J=9 9 Hz), 5.71 (1H, q, J=7, 6 Hz), 6.34 (1H, d, J=7 Hz), overlapping 6.36 (1H, d, J=6 Hz), 6.26 (1H, d, J=9 Hz), 7.43 (1H, q, 9, 2 Hz) overlapping 7.51 (1H, d, J=2 Hz), 7.75 (1H, d, J=9 Hz).

EXAMPLE 4

Trans-4-(N-Acetyl)ethylamino-6-cyano-3,4-dihydro-2,2-dimethyl-2H-benzo[b]pyran-3-yl acetate

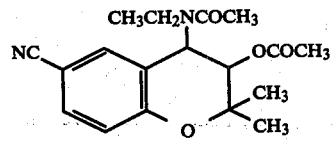

When the product of stirring 6-cyano-3,4-dihydro-2,2-dimethyl-3,4-epoxy-2H-benzo[b]pyran with ethanolic ethylamine was heated under reflux in acetic anhydride containing a little pyridine for 16 hours, the title compound was obtained after chromatography and recrystallisation from hexane-ethyl acetate as crystals of mp 125°–128° C.

IR (KBr disc) 2225, 1745, 1655 cm$^{-1}$

Anal. Calcd. for $C_{18}H_{22}N_2O_4$; C, 65.41; H, 6.71; N, 8.48.
Found: C, 64.97; H, 6.62; N, 8.39%.

EXAMPLE 5

Trans-4-(N-Acetyl)methylamino-6-cyano-3,4-dihydro-2,2-dimethyl-2H-benzo[b]pyran-3-ol

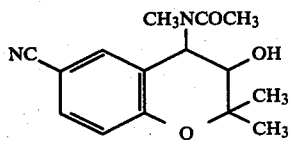   (5)

6-Cyano-3,4-dihydro-2,2-dimethyl-3,4-epoxy-2H-benzo[b]pyran (1.00 g) was stirred in ethanol (30 ml) containing 40% aqueous methylamine (1.96 g) for 3.75 days. Evaporation gave a gum which was dissolved in 2N hydrochloric acid and extracted with ether. The acid solution was basified with 10% sodium hydroxide solution and the liberated amine isolated via ethyl acetate.

The crude methylaminoalcohol (0.7 g) was stirred with anhydrous sodium acetate (1.4 g) in acetic anhydride (24 ml) at room temperature for 48 hours. A solid formed and this was collected by filtration. The filtrate was taken up in chloroform and washed several times with water and saturated sodium bicarbonate solution. The chloroform layer was dried over magnesium sulphate. After filtration and evaporation the solid residue was recrystallised from ethyl acetate to give the title compound (100 mg) as crystals of mp 197°–198° C.

Mass spectrum (EI) shows $M^+-H_2O$ at 256.1233

Anal. Calcd for $C_{17}H_{20}N_2O_3$: C,65.68; H,6.61,N,10.21. Found: C,65.60; H, 6.63; N, 10.13%.

EXAMPLE 6

Trans-4-N-Acetylamino-6-cyano-3,4-dihydro-2,2-dimethyl-2H-benzo[b]pyran-3-yl acetate

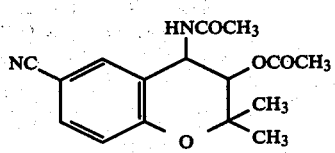   (6)

When the product of stirring 6-cyano-3,4-dihydro-2,2-dimethyl-3,4-epoxy-2H-benzo[b]pyran with ethanolic ammonium hydroxide was treated with anhydrous sodium acetate and acetic anhydride during 24 hours, at room temperature, the title compound was obtained as crystals of mp 181°–183° C. ethyl acetate.

| NMR (CDCl$_3$) δ | 1.33 (6H, s) |
|---|---|
| | 2.03 (3H, s) |
| | 2.09 (3H, s) |
| | 4.89 (1H, d, J = 9Hz) |
| | 5.22 (1H, t, J = 9, 9Hz) |
| | 6.07 (1H, d, J = 9Hz) |
| | 6.85 (1H, d, J = 8Hz) |
| | 7.32 (1H, q, J = 8, 2Hz) overlapping |
| | 7.37 (1H, d, J = 2Hz) |

EXAMPLE 7

Trans-4-N-Propionylamino-6-cyano-3,4-dihydro-2,2-dimethyl-2H-benzo[b]pyran-3-ol

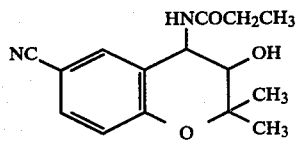   (7)

The product (0.46 g, obtained by stirring 6-cyano-3,4-dihydro-2,2-dimethyl-3,4-epoxy-2H-benzo[b]pyran with ethanolic ammonium hydroxide), and triethylamine (0.3 ml) were stirred in dichloromethane at 0° C. for 0.5 hr. Propionyl chloride (0.20 g) was added and the reaction mixture stirred for a further 0.5 hr. with cooling to 0° C. The reaction mixture was allowed to attain room temperature, and was washed with water and brine before drying over anhydrous magnesium sulphate. Removal of drying agent and evaporation left a solid which was recrystallised from ethyl acetate to give the title amide (147 mg) as crystals of mp 115°–117° C.

| NMR (CDCl$_3$) δ | 1.24 (3H, t, J = 8, 8Hz) |
|---|---|
| | 1.23 (3H, s) |
| | 1.50 (3H, s) |
| | 2.38 (2H, q, J = 8, 8, 8Hz) |
| | 3.65 (1H, d, J = 9Hz) |
| | 4.27 (1H exchangeable) |
| | 5.05 (1H, t, J = 9, 8Hz, collapsing to d, J = 9Hz on addition of D$_2$O) |
| | 6.13 (1H, d, J = 8Hz, exchangeable) |
| | 6.88 (1H, d, J = 8Hz) |
| | 7.45 (1H, q, J = 8, 2Hz) |
| | 7.55 (1H, d, J = 2Hz) |

EXAMPLE 8

Trans-4-N-Valerylamino-6-cyano-3,4-dihydro-2,2-dimethyl-2H-benzo[b]pyran-3-ol

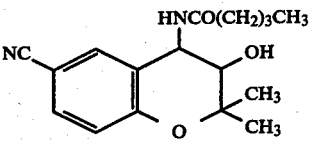   (8)

The product (0.51 g, obtained from the action of ethanolic ammonium hydroxide on 6-cyano-3,4-dihydro-2,2-dimethyl-3,4-epoxy-2H-benzo[b]pyran), and triethylamine (0.32 ml) were stirred in dichloromethane for 0.5 hr. at 0° C. Valeryl chloride (0.28 ml) was added and the reaction mixture stirred for a further 0.5 hr. at 0° C. The mixture was allowed to reach room temperature, and was washed with water and brine before drying over anhydrous magnesium sulphate. Removal of drying agent and solvent left a solid which was recrystallised from ethyl acetate-pentane to yield the title amide (0.24 g) as crystals of m.p. 158°–159° C.

| NMR (CDCl$_3$) δ | 0.95 (3H, irreg t) |
|---|---|
| | 1.26 (3H, s) and 1.50 (3H, s) overlapping 1.15–1.90 (4H, m) |
| | 2.34 (2H, irreg t, J = 7Hz) |
| | 3.61 (1H, d, J = 9Hz) |
| | 4.25 (1H, m) |

-continued

| | 5.05 (1H, t, J = 9, 8Hz) |
| --- | --- |
| | 6.08 (1H, d, J = 8Hz) |
| | 6.87 (1H, d, J = 8Hz) |
| | 7.44 (1H, q, J = 8, 2Hz) overlapped by |
| | 7.53 (1H, d, J = 2Hz) |

Anal. Calcd for $C_{17}H_{22}N_2O_3$: C, 67.53; H, 7.33; N, 9.26. Found: C, 67.84; H, 7.46; N, 9.51%.

EXAMPLE 9

Trans-4-N-Acetylamino-6-chloro-3,4-dihydro-2,2-dimethyl-2H-benzo[b]pyran-3-ol

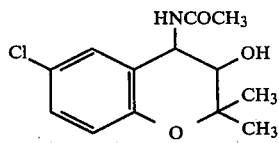

(9)

6-Chloro-3,4-dihydro-2,2-dimethyl-3,4-epoxy-2H-benzo[b]pyran (3.0 g), ammonium hydroxide solution (15.5 ml) and ethanol (6.0 ml) were stirred at room temperature for 3.75 days. Evaporation gave a solid which was taken up in ethyl acetate. The organic phase was extracted with 5N Hydrochloric acid, and the aqueous phase basified with 10% sodium hydroxide solution. Extraction with ethyl acetate, drying over anhydrous magnesium sulphate, filtration and evaporation gave the 4-amino-3-ol (1.74 g).

The crude aminoalcohol (0.5 g) and triethylamine (0.36 ml) were stirred in dichloromethane (15 ml) for 0.5 hr. Acetyl chloride (0.18 ml) was added in one portion with cooling to 0° C. and the reaction stirred vigorously for a further 0.5 hr. The reaction mixture was allowed to attain room temperature and was washed with water and brine, dried over anhydrous magnesium sulphate, filtered and evaporated. The crude solid so obtained was recrystallised from ethyl acetate to give the title amide (130 mg) as crystals of mp 186°–188° C.

| NMR (CDCl₃) δ | 1.23 (3H, s) |
| --- | --- |
| | 1.47 (3H, s) |
| | 2.15 (3H, s) |
| | 3.60 (1H, q, J = 9, 3Hz) |
| | 4.20 (1H, d, J = 3Hz) |
| | 4.97 (1H, t, J = 8, 8Hz) |
| | 5.85 (1H, m) |
| | 6.77 (1H, d, J = 9Hz) |
| | 7.05–7.30 (2H, m) |

EXAMPLE 10

Trans-6-Acetyl-4-N-acetylamino-3,4-dihydro-2,2-dimethyl-2H-benzo[b]pyran-3-ol

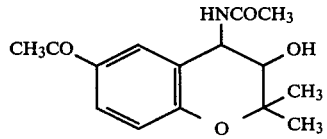

(10)

6-Acetyl-3,4-dihydro-2,2-dimethyl-3,4-epoxy-2H-benzo[b]pyran (2.0 g, prepared as described in example 1, of U.K. Pat. No. 1,511,187) was dissolved in ethanol (100 ml) and saturated with ammonia. The solution was stirred for 72 hours at room temperature. Evaporation gave a white solid which was subjected to the same acid-base treatment used to purify the 4-amino-3-ol of example 9.

The aminoalcohol so obtained (0.75 g) was stirred with triethylamine (0.44 ml) in dichloromethane (20 ml) for 0.5 hr. Acetylchloride (0.24 ml) was added in one portion with cooling to 0° C. to this solution, and stirring was continued for 0.5 hr. The solution was allowed to attain room temperature, and then washed with water and brine before drying over anhydrous magnesium sulphate. Filtration and evaporation gave a solid which was recrystallised from ethyl acetate-pentane to give the title compound (200 mg) as crystals of mp 182°–183° C.

| NMR (CDCl₃) δ | 1.25 (3H, s) |
| --- | --- |
| | 1.47 (3H, s) |
| | 1.18 (3H, s) |
| | 2.30 (3H, s) |
| | 3.60 (1H, q, J = 9, 5Hz) |
| | 4.96 (1H, t, J = 9, 9Hz) |
| | 5.21 (1H, d, J = 5Hz) |
| | 6.78 (1H, d, J = 8Hz) |
| | 7.76 (1H, q, J = 8, 3Hz) overlapped by |
| | 7.83 (1H, d, J = 3Hz) |
| | 8.04 (1H, d, J = 9Hz) |

Mass Spectrum (EI) shows M+ at M/Z 277.1311 Calcd for $C_{15}H_{19}NO_4$: 277.1314.

EXAMPLE 11

Trans-4,6-bis(Acetylamino)-3,4-dihydro-2,2-dimethyl-7-nitro-2H-benzo[b]pyran-3-ol

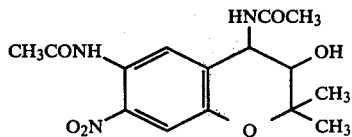

(11)

The compound of description 6 (210 mg), sodium hydroxide pellets (30 mg), water (2.5 ml) and chloroform (7 ml) were stirred together before addition of acetyl chloride (58 mg). The reaction mixture was stirred for 0.5 hr. before addition of water (10 ml) and chloroform (10 ml) and separation of the layers. The aqueous layer was further extracted with chloroform and the organic layers combined and dried over anhydrous magnesium sulphate. Removal of drying agent and solvent gave a yellow-orange solid which was recrystallised from ethyl acetate to give the title compound (45 mg) mp 244°–246° C.

| NMR (CDCl₃ – DMSO d₆) δ | 1.23 (3H, s) |
| --- | --- |
| | 1.45 (3H, s) |
| | 2.03 (3H, s) |
| | 2.09 (3H, s) |
| | 3.60 (1H, q, J = 9, 5Hz) |
| | 4.87 (1H, t, J = 9, 9Hz) |
| | 5.37 (1H, d, J = 5Hz) |
| | 7.30 (1H, s) |
| | 7.58 (1H, s) |
| | 8.17 (1H, d, J = 9Hz) |
| | 9.84 (1H, s) |

Mass spectrum (EI) shows M+ at M/Z 337.1279. Calcd. for $C_{15}H_{19}N_3O_6$: 337.1274.

EXAMPLE 12

Trans-4,7-bis(Acetylamino)-3,4-dihydro-2,2-dimethyl-6-nitro-2H-benzo[b]pyran-3-ol

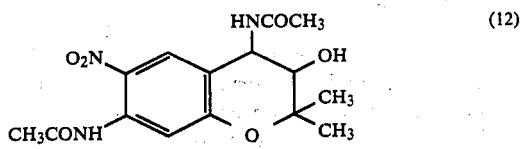

(12)

The compound of description 7 (90 mg) and triethylamine (0.04 ml) were stirred in dichloromethane (10 ml) for 0.5 hr. at room temperature. Acetyl chloride (0.02 ml) was added to the reaction mixture with cooling to 0° C., and stirring continued for 0.5 hr. after addition. After the reaction mixture had reached room temperature, the organic phase was washed with water, dried over anhydrous magnesium sulphate and evaporated. The residue was recrystallised from ethyl acetate to give the title compound (24 mg) as crystals of mp 256°–259° C.

Mas spectrum (EI): $M^+-H_2O$ at M/Z 319.1171. Calcd for $C_{15}H_{17}N_3O_5$: 319.1168.

EXAMPLE 13

Trans-4-Chloroacetylamino-6-cyano-3,4-dihydro-2,2-dimethyl-2H-benzo[b]-pyran-3-ol

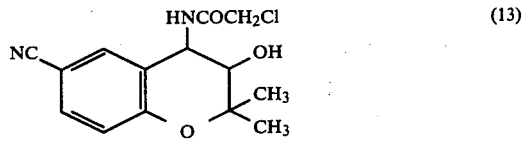

(13)

The amino alcohol (4.0 g, obtained by stirring 6-cyano-3,4-dihydro-2,2-dimethyl-3,4-epoxy-2H-benzo[b]pyran with ethanolic ammonium hydroxide), and triethylamine (2.55 ml) were stirred in dichloromethane (120 ml) for 0.5 hr. Chloroacetyl chloride (1.46 ml) was added in one portion with cooling to 0° C., and the reaction mixture stirred for a further 0.5 hr. before being allowed to attain room temperature. The reaction mixture was washed with water, brine, and dried over anhydrous magnesium sulphate. The solution was filtered and evaporated to give a grey coloured solid. Two recrystallisations from ethyl acetate gave the title compound (1.48 g) of m.p. 196°–197° C.

| NMR (CDCl$_3$ + DMSO d$_6$) δ | 1.38 (3H, s) |
| --- | --- |
| | 1.51 (3H, s) |
| | 3.60 (1H, d, J = 9Hz) |
| | 4.14 (2H, s) |
| | 4.90 (1H, t, J = 9, 9Hz) |
| | 6.81 (1H, d, J = 9, Hz) |
| | 7.30–7.57 (2H, m) |
| | 8.46 (1H, d, J = 9Hz). |

EXAMPLE 14

4-Acetylamino-6-cyano-2,2-dimethyl-2H-benzo[b]pyran

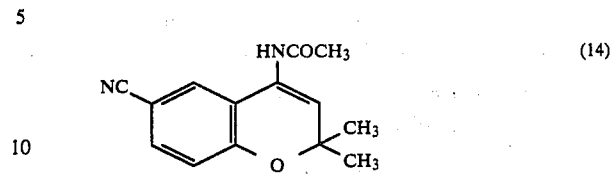

(14)

The compound of example 2, (0.5 g) and sodium hydride (0.058 g, 80% dispersion in oil) were heated under reflux in dry xylene (50 ml) in an atmosphere of nitrogen for 48 hours. After cooling, water (25 ml) was added cautiously, and the layers separated. The organic phase was washed with water and brine, and dried over anhydrous magnesium sulphate. Filtration and evaporation gave a gum which was chromatographed (chromatotron, gradient elution: ethyl acetate-pentane, 2 mm silica gel, 6 ml/min) to give the title compound (230 mg) in the initial fractions, as needles (65 mg) from diethyl ether, having a m.p. of 146°–147° C.

| NMR (CDCl$_3$) δ | 1.50 (6H, s) |
| --- | --- |
| | 2.23 (3H, s) |
| | 6.37 (1H, s) |
| | 6.90 (1H, d, J = 9Hz) overlapping 7.00 (1H, m) |
| | 7.45 (1H, q, J-9, 2Hz) overlapping 7.52 (1H, d, J = 2Hz) |

EXAMPLE 15

Trans-6-cyano-3,4-dihydro-4-methoxyacetylamino-2,2-dimethyl-2H-benzo[b]pyran-3-ol

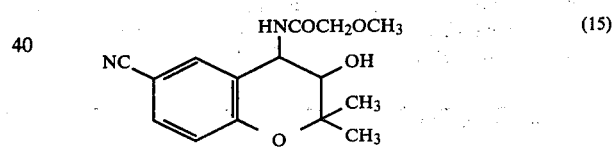

(15)

The aminoalcohol (4.37 g, obtained by stirring 6-cyano-3,4-dihydro-2,2-dimethyl-3,4-epoxy-2H-benzo[b]pyran with ethanolic ammonium hydroxide), and triethylamine (2.79 ml) were stirred in dichloromethane (30 ml) for 0.5 hr. The stirred solution was cooled to 0° C. and methoxyacetyl chloride (2.18 g) was added in one portion and the reaction mixture stirred for a further 0.75 hr, and then allowed to reach room temperature. The reaction mixture was washed with water, brine, and dried over anhydrous magnesium sulphate. The solution was filtered and evaporated to give a solid which was recrystallised from ethyl acetate to give the title compound (3.01 g) of mp 162°–163° C.

| NMR (CDCl$_3$) δ | 1.30 (3H, s) |
| --- | --- |
| | 1.52 (3H, s) |
| | 3.48 (3H, s) |
| | 3.67 (1H, d, J = 9Hz) |
| | 4.07 (2H, s) |
| | 5.10 (1H, t, J = 9, 9Hz) collapsing to doublet, J = 9Hz on addition of D$_2$O, |
| | 6.93 (1H, d, J = 9Hz) overlapping |
| | 6.95–7.00 (1H, m, exchangeable) |
| | 7.50 (1H, q, J = 9, 2Hz) overlapped by |

7.55 (1H, d, J = 2Hz).

EXAMPLE 16

Trans-6-cyano-3,4-dihydro-2,2-dimethyl-4-thi-oacetylamino-2H-benzo[b]pyran-3-ol

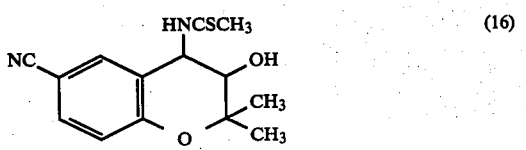
(16)

The compound of example 2 (520 mg) and Lawesson's reagent (444 mg) were heated under reflux in dry toluene for 1 hr. Evaporation gave a foam which was chromatographed on 45 g of silica gel using chloroform containing up to 10% ethanol in a gradient elution. Fractions containing the desired material (0.64 g) were combined and rechromatographed using a chromatotron (2 mm silica gel, flow rate 9 ml/min of chloroform) to give a crude product (110 mg) which on trituration with hexane gave the title compound as a yellow solid (68 mg) of mp 176°–180° C.

EXAMPLE 17

Trans-6-cyano-4-formylamino-3,4-dihydro-2,2-dimethyl-2H-benzo[b]pyran-3-ol

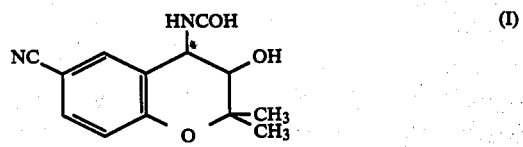
(I)

The aminoalcohol (0.9 g), obtained by stirring 6-cyano-3,4-dihydro-2,2-dimethyl-3,4-epoxy-2H-benzo[b]pyran with ethanolic ammonium hydroxide), was heated under reflux in formic acid (15 ml) and pyridine (1 ml) during 19 hr. The cooled solution was poured into water and extracted with ethyl acetate. The organic layer was washed with water and dried over anhydrous magnesium sulphate. Filtration and evaporation left an orange coloured oil which was chromatographed (chromatotron, ethyl acetate-pentane gradient elution on silica gel 2 mm, flow rate 9 ml/min.) to give after one recrystallisation from ethyl acetate, the title compound (220 mg), of m.p. 228.5°–230.5° C.

Mass spectrum M+ AT M/Z 246.0992.
Calcd for $C_{13}H_{14}N_2O_3$ 246.1004.

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). W+W BP recorder, model 8005, was used to display pulses. Prior to all measurements rats were placed in a heated environment (33.5±0.5° C.) before transfer to a restraining cage. Each determination of blood pressure was the mean of at least 6 readings. Spontaneously hypertensive rats (ages 12–18 weeks) with systolic blood pressures 170 mmHg were considered hypertensive.

| Compound 1 of Example 1 | Time Post Dose (Hours) | % Change in Systolic Blood Pressure | % Change in Heart Rate |
|---|---|---|---|
| 6 rats Dose 1 mg/kg po Initial Blood Pressure 234 ± 7 mmHg Initial Heart Rate 467 ± 19 beats/min | 1 | −22 ± 5 | −6 ± 7 |
| | 2 | −19 ± 3 | −2 ± 3 |
| | 4 | −13 ± 2 | −6 ± 3 |
| | 6 | −27 ± 4 | −7 ± 4 |
| | 24 | −7 ± 4 | −6 ± 1 |

| Compound 2 of Example 2 | Time Post Dose (Hours) | % Change in Systolic Blood Pressure | % Change in Heart Rate |
|---|---|---|---|
| 6 rats Dose 0.3 mg/kg po Initial Blood Pressure 199 ± 6 mmHg Initial Heart Rate 502 ± 8 beats/min | 1 | −47 ± 5* | 0 ± 4 |
| | 2 | −38 ± 4* | 1 ± 4 |
| | 4 | −35 ± 2** | −4 ± 5 |
| | 6 | −30 ± 1 | −10 ± 4 |
| | 24 | −10 ± 5 | −1 ± 1 |

*1 rat had no measurable pulse.
**2 rats had no measurable pulse.

TOXICITY

No toxic effects were observed in the above test.
What we claim is:
1. A compound of formula (I):

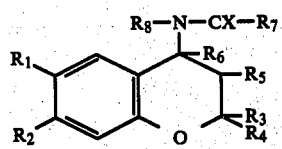
(I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ are $C_{2-5}$ polymethylene;

either $R_5$ is hydroxy, $C_{1-6}$ alkoxy or $C_{2-7}$ unsubstituted carboxylic acyloxy and $R_6$ is hydrogen or $R_5$ and $R_6$ together are a bond;

$R_7$ is hydrogen, $C_{1-6}$ alkyl or $C_{2-6}$ alkenyl;

$R_8$ is hydrogen or $C_{1-6}$ alkyl; and

X is oxygen or sulphur; the $R_8$—N—CX—$R_7$ group being trans to the $R_5$ group when $R_5$ and $R_6$ together are not a bond; or, when one or the other of $R_1$ and $R_2$ is an amino or an amino-containing group, a pharmaceutically acceptable salt thereof.

2. A compound according to claim 1, wherein one of $R_1$ and $R_2$ is hydrogen, the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro or cyano.

3. A compound according to claim 2, wherein $R_2$ is hydrogen.

4. A compound according to claim 1, wherein one of $R_1$ and $R_2$ is nitro, cyano or $C_{1-3}$ alkylcarbonyl and the other is amino optionally substituted by one or two $C_{1-6}$ alkyl or by $C_{2-7}$ alkanoyl.

5. A compound according to claim 4, wherein one of $R_1$ and $R_2$ is nitro or cyano and the other is amino.

6. A compound according to claim 4, wherein $R_1$ is nitro, cyano or $C_{1-3}$ alkylcarbonyl.

7. A compound according to claim 1, wherein the alkyl groups or alkyl moieties of alkyl-containing groups for $R_1$ or $R_2$ are methyl or ethyl.

8. A compound according to claim 1, wherein $R_3$ and $R_4$ are both $C_{1-4}$ alkyl.

9. A compound according to claim 8, wherein $R_3$ and $R_4$ are both methyl.

10. A compound according to claim 1, wherein $R_5$ is hydroxy or $C_{2-7}$ unsubstituted carboxylic acyloxy and $R_6$ is hydrogen.

11. A compound according to claim 1, wherein $R_5$ and $R_6$ together are a bond.

12. A compound according to claim 1, wherein $R_7$ is hydrogen or $C_{1-6}$ alkyl.

13. A compound according to claim 12, wherein $R_7$ is hydrogen, methyl or ethyl.

14. A compound according to claim 1, wherein $R_8$ is hydrogen or methyl.

15. A compound according to claim 14, wherein $R_8$ is hydrogen.

16. Trans-4-(N-acetyl)ethylamino-6-cyano-3,4-dihydro-2,2-dimethyl-2H-benzo[b]pyran-3-ol;
trans-6-cyano-3-,4-dihydro-2,2-dimethyl-4-N-propenoylamino-2H-benzo[b]pyran-3-ol;
trans-4-(N-acetyl)ethylamino-6-cyano-3,4-dihydro-2,2-dimethyl-2H-benzo[b]pyran-3-yl acetate;
trans-4-(N-acetyl)methylamino-6-cyano-3,4-dihydro-2,2-dimethyl-2H-benzo[b]pyran-3-ol;
trans-4-N-propionylamino-6-cyano-3,4-dihydro-2,2-dimethyl-2H-benzo[b]pyran-3-ol;
trans-4-N-valerylamino-6-cyano-3,4-dihydro-2,2-dimethyl-2H-benzo[b]pyran-3-ol;
trans-4-N-acetylamino-6-chloro-3,4-dihydro-2,2-dimethyl-2H-benzo[b]pyran-3-ol;
trans-4,6-bis(acetylamino)-3,4-dihydro-2,2-dimethyl-7-nitro-2H-benzo[b]pyran-3-ol;
trans-4,6-bis(acetylamino)-3,4-dihydro-2,2-dimethyl-7-nitro-2H-benzo[b]pyran-3-ol;
trans-4,7-bis(acetylamino)-3,4-dihydro-2,2-dimethyl-6-nitro-2H-benzo[b]pyran-3-ol;
4-acetylamino-6-cyano-2,2-dimethyl-2H-benzo[b]pyran;
trans-4-thioacetylamino-6-cyano-3,4-dihydro-2,2-dimethyl-2H-benzo[b]pyran-3-ol; or
trans-4-formylamino-2,2-dimethyl-3,4-dihydro-2H-benzo[b]pyran-3-ol.

17. Trans-4-N-acetylamino-6-cyano-3,4-dihydro-2,2-dimethyl-2H-benzo[b]pyran-3-ol;
trans-4-N-acetylamino-6-cyano-3,4-dihydro-2,2-dimethyl-2H-benzo[b]pyran-3-yl acetate;
trans-4-N-acetylamino-6-acetyl-3,4-dihydro,2,2-dimethyl-2H-benzo[b]pyran-3-ol; or
trans-4,7-bis(acetylamino)-6-nitro-3,4-dihydro-2,2-dimethyl-2H-benzo[b]pyran-3-ol.

18. A compound according to claim 1, in substantially pure form.

19. A pharmaceutical composition for the treatment of hypertension in mammals, including man, which comprises an effective amount of a compound of formula (I), as defined in claim 1, and a pharmaceutically acceptable carrier.

20. A method of treating hypertension in mammals including man, which comprises administering to the hypertensive mammal an anti-hypertensive effective amount of a compound of formula (I), as defined in claims 1.

* * * * *